United States Patent
Koga et al.

(10) Patent No.: US 7,109,013 B2
(45) Date of Patent: Sep. 19, 2006

(54) CELLULASE PREPARATION CONTAINING NONIONIC SURFACTANT AND METHOD OF TREATING FIBER

(75) Inventors: Jinichiro Koga, Saitama (JP); Akitaka Nakane, Saitama (JP); Yuko Baba, Saitama (JP); Toshiaki Kono, Saitama (JP)

(73) Assignee: Meiji Seika Kaisha, Ltd., Tokyo (JP)

( * ) Notice: Subject to any disclaimer, the term of this patent is extended or adjusted under 35 U.S.C. 154(b) by 450 days.

(21) Appl. No.: 10/416,328

(22) PCT Filed: Nov. 12, 2001

(86) PCT No.: PCT/JP01/09858

§ 371 (c)(1),
(2), (4) Date: May 8, 2003

(87) PCT Pub. No.: WO02/38754

PCT Pub. Date: May 16, 2002

(65) Prior Publication Data

US 2004/0038841 A1    Feb. 26, 2004

(51) Int. Cl.
*C12N 9/24*      (2006.01)
*C12N 1/20*      (2006.01)
*C12N 15/00*     (2006.01)
*C07H 21/04*     (2006.01)

(52) U.S. Cl. ............... 435/200; 435/252.3; 435/320.1; 536/23.2

(58) Field of Classification Search ................ 435/200, 435/252.3, 320.1; 536/23.2
See application file for complete search history.

(56) References Cited

U.S. PATENT DOCUMENTS 6,921,655 B1 *   7/2005   Nakamura et al. .......... 435/200

FOREIGN PATENT DOCUMENTS

| EP | 0 843 041 A1 | 5/1998 |
|---|---|---|
| EP | 1123974 A1 | 8/2001 |
| JP | 60-210984 A | 10/1985 |
| JP | 60-226599 A | 11/1985 |

* cited by examiner

*Primary Examiner*—Tekchand Saidha
(74) *Attorney, Agent, or Firm*—Posz Law Group, PLC; R. Eugene Varndell, Jr.

(57) ABSTRACT

The present invention relates to a cellulase preparation comprising nonionic surfactants together with endoglucanases derived from Zygomycetes; a detergent composition comprising the above cellulase preparation with detergent components; a method of treating fabric which comprises treating cellulose-containing fabric with the above cellulase preparation so as to improve the properties of the fabric; a method of deinking waster paper which comprises a step of treating waste paper with the above cellulase preparation together with a deinking agent; and a method of improving the freeness of paper pulp which comprises a step of treating paper pulp with the above cellulase preparation.

30 Claims, No Drawings

CELLULASE PREPARATION CONTAINING NONIONIC SURFACTANT AND METHOD OF TREATING FIBER

TECHNICAL FIELD

The present invention relates to a cellulase preparation comprising a nonionic surfactant(s) by which endoglucanase activity has improved; a detergent comprising the cellulase preparation; and a method of treating fabric, which uses the cellulase preparation.

BACKGROUND ART

Cellulase has three types of enzyme activities: cellobiohydrolase activity which hydrolyzes the solid crystal regions of cellulose from the nonreduced end in an exo manner so as to generate cellobiose; endoglucanase activity which hydrolyzes the amorphous regions of cellulose in an endo manner so as to make cellulose molecules into low molecular weight molecules and to generate various types of cellooligosaccharides; and β-glucosidase activity which decomposes cellobiose or cellooligosaccharide into glucose. Of the enzymes, when endoglucanase exerts high activity, cellulase is advantageously used to treat fabric.

To impart certain desired properties to cellulose-containing fabric, the fabric has conventionally been treated with cellulase. For example, in the textile industry, treatment with cellulase is carried out to improve the touch and appearance of cellulose-containing fabric, or to impart "stonewash" appearance to colored cellulose-containing fabric thereby providing the fabric with localized color variation (EP Patent No. 307,564).

It is known that fuzz is developed on colored cellulose-containing fabric by repeated washing and that it blurs the color of the colored fabric. A cellulase-containing detergent removes such fuzz and makes the color of the fabric clear (color clarification) (EP Patent No. 220,016), and therefore detergents containing cellulase are currently on the market mainly in Europe and the United States.

In such textile processing, cellulase derived from wood-rotting fungi such as *Trichoderma* and *Humicola* is mainly used. Such cellulase is used as a mixture comprising multiple cellulase components which is obtained by processing a culture filtrate of microorganisms having cellulolytic activity. However, in order to achieve greater economy, a cellulase preparation obtained by isolating from cellulase components, only endoglucanase which largely acts on fabric treatment, and genetically enhancing it, has recently been used. Examples of such endoglucanase with high activity include: EGV (JP Patent Publication (PCT Translation) No. 5-509223) and NCE4 (WO98/03640) derived from *Humicola insolens*, which strongly act on cotton fabrics; RCE I, RCE II and RCE III derived from *Rhizopus oryzae*, which strongly act on lyocell fabrics; MCE I and MCE II derived from *Mucor circinelloides*; and PCE I derived from *Phycomyces nitens* (WO00/24879).

In order to improve the effects of cellulase, the combined use of additives has also been attempted. For example, JP Patent Publication (PCT Translation) No. 5-507615 describes that a water-soluble polymer such as polyvinylpyrrolidone, polyvinyl alcohol and polyacrylamide enhances the effects of *Humicola insolens*-derived cellulase and improves its activity of removing fuzz from colored fabric. Moreover, it is known that CMCase activity in the culture solution of *Trichoderma viride* is improved by the addition of Tween 20 (Ooshima, H. et al., Biotechnology and Bioengineering 28: 1727–1734, 1986).

However, the cellulases used for the above-described purposes are all expensive. Therefore, in order to achieve an industrial level application, further improvement of endoglucanase activity is desired, so that the above effects of cellulase can be more efficiently exerted.

DISCLOSURE OF THE INVENTION

It is therefore the object of the present invention to provide a cellulase preparation having improved endoglucanase activity, which can be used for the purpose that the fabric treatment for improving cellulose-containing fabric such as the removal of fuzz can be carried out efficiently and economically.

As a result of intensive studies directed towards the above object, the present inventors have found that a nonionic surfactant enhances the effects of Zygomycetes-derived endoglucanases such as RCE I, MCE I and PCE I, at rates far higher than *Trichoderma*- or *Humicola*-derived endoglucanase, thereby completing the present invention.

That is to say, the present invention relates to the following (1) to (5):

(1) A cellulase preparation comprising nonionic surfactant(s) together with endoglucanase(s) derived from Zygomycetes, (2) A detergent composition obtained by blending said cellulase preparation with detergent components, (3) A method of treating fabric which comprises treating cellulose-containing fabric with said cellulase preparation so as to improve the properties of the fabric, (4) A method of deinking waste paper comprising a step of treating waste paper with said cellulase preparation together with a deinking agent, and (5) A method of improving the freeness of paper pulp comprising a step of treating paper pulp with said cellulase preparation.

[1] Cellulase Preparation

The cellulase preparation of the present invention comprises endoglucanase(s) derived from Zygomycetes, and nonionic surfactant(s).

In the present invention, the term, endoglucanase, is used to mean endo-1,4-β-glucanase EC3.2.1.4, and it has the activity to hydrolyze β-1,4-glucopyranosil bonds of β-1,4-glucan.

Examples of endoglucanases derived from Zygomycetes used in the present invention include endoglucanases derived from *Rhizopus* sp., *Phycomyces* sp. or *Mucor* sp. Specific examples of such endoglucanases used herein include RCE I, RCE II, RCE III, MCE I, MCE II and PCE I proteins having amino acid sequences as shown in SEQ ID NOS: 1 to 6, respectively, which are disclosed in WO00/24879.

RCE I, II and III are derived from the *Rhizopus oryzae* CP96001 strain, which has been deposited under the terms of the Budapest Treaty with the National Institute of Advanced Industrial Science and Technology, at the an Independent Administrative Institution under the Ministry of Economy, Trade and Industry, AIST Tsukuba Central 6, Higashi 1-1-1, Tsukuba, Ibaraki, Japan (postal code No. 305-8566), [the former name: the National Institute of Bioscience and Human-Technology, Agency of Industrial Science and Technology, the former address: Higashi 1-1-3, Tsukuba, Ibaraki, Japan] under accession No. FERM BP-6889 on Apr. 21, 1997. MCE I and II are derived from the *Mucor circinelloides* CP99001 strain, which has been deposited with the same international depositary authority, that is, the National Institute of Advanced Industrial Science and Technology, an Independent. Administrative Institution under the Ministry of Economy, Trade and Industry, at the AIST Tsukuba Central 6, Higashi 1-1-1, Tsukuba, Ibaraki, Japan (postal code No. 305-8566), [the former name: the National Institute of Bioscience and Human-Technology, Agency of Industrial Science and Technology, the former address: Higashi 1-1-3, Tsukuba, Ibaraki, Japan] under accession No. FERM BP-6890 on Jul. 2, 1999. Moreover, PCE I was derived from the *Phycomyces nitens* CP99002 strain, which has been deposited with the same international depositary authority under accession No. FERM BP-6891 on Jul. 2, 1999.

In the present invention, the above-stated RCE I, RCE II, RCE III MCE I, MCE II and PCE I proteins include modified proteins and homologues thereof. The term "modified protein" is used herein to mean a protein having an amino acid sequence comprising an addition, insertion, deletion or substitution of one or more amino acids (for example, one to several tens of, specifically, one to approximately fifty, preferably, one to approximately thirty, and more preferably, one to approximately nine amino acids) with respect to the amino acid sequence of each of the above mentioned RCE I, RCE II, RCE III, MCE I, MCE II and PCE I, and having endoglucanase activity. The term "homologue" is used herein to mean a protein having an amino acid sequence encoded by a gene (nucleotide sequence) complementary to a gene (nucleotide sequence) "hybridizing under stringent conditions" with a gene (nucleotide sequence) encoding the amino acid sequence of each of the above mentioned RCE I, RCE II, RCE III, MCE I, MCE II and PCE I, and having endoglucanase activity. Herein, the term "under stringent conditions" is used to mean conditions in which a probe comprising a nucleotide sequence encoding a part or all of the amino acid sequences of RCE I, RCE II, RCE III, MCE I, MCE II or PCE I, or the amino acid sequences of modified proteins thereof would hybridize with a gene encoding a homologue, but the same probe does not hybridize with an endoglucanase NCE 4 gene (SEQ ID NO: 7) as disclosed in WO98/03640 or endoglucanase SCE 3 gene (SEQ ID NO: 8) as disclosed in WO98/54322 (it should be noted that the amount of DNA used herein is equivalent to the amount of each of the NCE 4 gene, the SCE 3 gene and a gene encoding the homologue.) More specifically, it means conditions in which, using as a probe a full-length DNA sequence encoding the amino acid sequence of labeled RCE I, pre-hybridization is carried out at 42° C. for 1 hour according to the method of the ECL direct DNA/RNA labeling and detection system (Amersham), then the above probe is added thereto followed by hybridization at 42° C. for 15 hours, and thereafter, the resultant product is washed twice with a solution containing 0.4% SDS, 6 M urea and 0.5×SSC (SSC; 15 mM trisodium citrate, 150 mM sodium chloride) at 42° C. for 20 minutes, and finally followed by washing the product twice with 5×SSC at room temperature for 10 minutes.

An example of such a modified protein or homologue includes a protein comprising an amino acid sequence having preferably 80% or more homology, more preferably 90% or more homology, further more preferably 95% or more homology, and most preferably 98% or more homology with the amino acid sequence of RCE I, RCE II, RCE III, MCE I, MCE II or PCE I. The above-stated values of homology may be calculated by a homology search program which is well known to a person skilled in the art, but the values are preferably calculated using a default (initialized) parameter of FASTA3 [Science, 227, 1435–1441 (1985); Proc. Natl. Acad. Sci. USA, 85, 2444–2448 (998)

The nonionic surfactant included in the cellulase preparation of the present invention means a surfactant whose hydrophilic group is a nonionic group. Examples of such a nonionic surfactant include polyoxyethylene alkylether, polyoxyethylene alkylphenylether, polyoxyethylene monofatty acid ester, polyoxyethylene sorbitan monofatty acid ester, sorbitan monofatty acid ester, polyethylene glycol, glycerol monofatty acid ester, polyglycerine fatty acid ester, alkyl glycoside, esters of polyethoxylated alkyl glycosides, alkyl dimethyl amine oxide, fatty acid diethanol amide, polyoxyethylene alkylamine, terephthalic acid tetraethylene glycol polymer, alkyl polyethylene glycol ether, nonyl phenol polyethylene glycol ether, and fatty acid ester of sucrose or glucose. These nonionic surfactants can be used alone or in combination with other nonionic surfactants.

Moreover, the cellulase preparation of the present invention may comprise components which are conventionally contained in cellulase preparations such as excipients and preservatives. The form of the cellulase preparation may be solid or liquid, and specific examples of the form include powder, particulate, granule, non-dusting granule and liquid formulation.

A non-dusting granule that is one form of cellulase preparation can be produced according to the common dry granulation method. That is to say, powder cellulase enzyme is mixed with one or several types selected from a group comprising inorganic salts such as sodium sulfate and sodium chloride which are neutral and do not have an effect on endoglucanase activity; minerals such as bentonite and montmorillonite which do not have an effect on endoglucanase activity; and neutral organic matters such as starch and powder cellulose. Thereafter, the powders or the finely suspended suspension of one or several types of the above-described nonionic surfactants which improve the effects of endoglucanase are added to the mixture, and the thus obtained product is then fully mixed or kneaded. Depending on the situation, a synthetic polymer such as polyethylene glycol and natural polymer such as starch, which binds solids, is optionally added to the mixture and further kneaded. Thereafter, granulation is carried out by extrusion molding, using, for example, a disk pelleter, and the obtained molded material is then converted into a spherical form using a marumerizer followed by drying, so that non-dusting granules can be produced. Naturally, it is also possible to coat the surface of granules with a polymer or the like to control the permeation of oxygen or water. This time, one or multiple nonionic surfactants which improve the effect of endoglucanase are added to the above cellulase preparation at a ratio of 0.1 to 50% by weight, preferably 0.1 to 30% by weight, and more preferably 1 to 20% by weight.

On the other hand, the liquid preparation can be prepared by blending an endoglucanase stabilizer such as a synthetic and natural polymer with a cellulase solution, and adding inorganic salts or a synthetic preservative, as necessary. This time, one or multiple nonionic surfactants which improve the effect of endoglucanase can also be added. As in the case of the non-dusting granule, one or multiple nonionic surfactants which improve the effect of endoglucanase are added to the above cellulase preparation at a ratio of 0.01 to 50% by weight, preferably 0.1 to 30% by weight, and more preferably 1 to 20% by weight.

[2] Detergent Composition

The above described cellulase preparation of the present invention is blended with known detergent components such as builders, bleaching agents, bleaching activators, corrosion inhibitors, sequestering agents, stain dissociating polymers, aromatics, other enzymes, enzyme stabilizers, formulation assistants, fluorescent brightening agents and foaming promoters so that a detergent composition can be produced.

The present detergent composition relates to the granular soil removal, the color clarification, the defuzzing, the depilling and the reduction of stiffness, and these can be improved by the composition of the present invention.

[3] Method of Treating Fabric

The method of treating fabric of the present invention comprises treating cellulose-containing fabric with the above cellulase preparation.

The following properties of cellulose-containing fabric can be improved by the present fabric treatment method:
(1) Removal of fuzz (reduction of the rate of the formation of fuzz, and reduction of fuzz),
(2) Color clarification of colored cellulose-containing fabric,
(3) Providing of localized color variation to colored cellulose-containing fabric, that is, providing of stonewash-like appearance and texture to colored cellulose-containing fabric, typically jeans,
(4) Enhancement of the touch and appearance of fabric by reducing weight, and
(5) Softening of fabric (reduction of stiffness).

The above method of treating fabric can be carried out typically during washing, but it can also be carried out during soaking or rinsing. Specifically, the method of treating fabric of the present invention can be carried out by adding the cellulase preparation of the present invention into water in which fabric is or will be soaked.

Conditions such as contact temperature and the amount of endoglucanase may appropriately be determined, taking into consideration various other conditions. For example, in the case of reducing the rate of the formation of fuzz or reducing fuzz of the cellulose-containing fabric, the fabric can be treated at a temperature of approximately 30° C. to 60° C., using 10 to 10,000 mg/L of nonionic surfactants and endoglucanases in a protein concentration of 0.05 to 20 mg/L.

In the case of providing the colored cellulose-containing fabric with localized color variations, the fabric can be treated at a temperature of approximately 30° C. to 60° C., using 10 to 10,000 mg/L of nonionic surfactants and endoglucanases in a protein concentration of 0.1 to 30 mg/L.

In a processing of reducing weight which is directed towards the improvement of the touch and appearance of the cellulose-containing fabric, the fabric can be treated at a temperature of approximately 30° C. to 60° C., using 10 to 10,000 mg/L of nonionic surfactants and endoglucanases in a protein concentration of 0.2 to 50 mg/L.

In any of the above cases, the nonionic surfactant may be dissolved or suspended in water.

The protein concentration of each type of endoglucanase is measured by HPLC analysis using TSKgel TMS-250 column (4.6 mm I.D.×75 cm) (TOSOH Corporation). The HPLC analysis involves loading acetonitrile in 0.05% TFA (trifluoroacetic acid) with a linear concentration gradient of 0% to 80% at a flow rate of 1.0 ml/min so as to elute each type of endoglucanase, and calculating the protein concentration from the peak area at UV 280 nm. A purified NCE4, the protein concentration of which is previously determined by a Protein Assay Kit (BioRad Laboratories), is subjected to the HPLC analysis in the same manner as above, so that it is used as a standard. According to the method described in International Publication No. WO98/03640, the purified NCE4 is obtained by culturing Humicola insolens [Humicola insolens MN200-1 which was deposited under accession No. FERM BP-5977 (original accession No. FERM-15736, original accession date: Jul. 15, 1996) with the National Institute of Advanced Industrial Science and Technology, at the an Independent Administrative Institution under the Ministry of Economy, Trade and Industry, AIST Tsukuba Central 6, Higashi 1-1-1, Tsukuba, Ibaraki, Japan (postal code No. 305-8566), the former name: the National Institute of Bioscience and Human-Technology, Agency of Industrial Science and Technology], and purifying the obtained culture. As a standard for the determination of a protein concentration in the Protein Assay Kit, Albumin Standard (Bovin serum albumin, fraction V, PIERCE) is used.

[4] Method of Deinking Waste paper

The method of deinking waste paper of the present invention comprises treating waste paper with the above-described cellulase preparation together with a deinking agent.

Specifically, the present method can be carried out by treating waste paper with the cellulase preparation of the present invention together with a deinking agent in a deinking step in a process of producing recycled paper from waste paper. The present method enables the deinking of waste paper, thereby improving the whiteness of waste paper. Waste paper which is the target of the present method include all types of common waste paper such as used news paper, used magazine paper and low to middle grade of printed used paper comprising mechanical pulp and/or chemical pulp; used wood-free paper comprising chemical pulp; and printed waste paper thereof such as coating paper. The above-described deinking agent means an agent used in the deinking of waste paper, and examples of such a deinking agent include alkali such as sodium chloride and sodium carbonate, sodium silicate, hydrogen peroxide, phosphate, anionic or nonionic surfactant, scavenger such as oleic acid, assistant agents such as pH stabilizer, chelating agent and dispersing agent, and others.

[5] Method of Improving Freeness of Paper Pulp

The method of improving the freeness of paper pulp of the present invention comprises treating paper pulp with the above-described cellulase preparation.

Specifically, the present method can be carried out by treating paper pulp with the cellulase preparation of the present invention. Examples of paper pulp which can be the target of the present method include waste paper pulp, recycled paperboard pulp, kraft pulp, sulfite pulp, thermo-mechanical treatment pulp, and other high-yield pulp.

This specification includes the contents as disclosed in the specification of Japanese Patent Application No. 2000-343921, which is a priority document of the present application.

BEST MODE FOR CARRYING OUT THE PRESENT INVENTION

The present invention is further described in the following examples. However, the examples are provided for illustrative purposes only, and are not intended to limit the scope of the invention.

Hereinafter, the term "endoglucanase activity" means CMCase activity. Moreover, regarding the "CMCase activity," when a solution comprising cellulase enzyme and carboxymethylcellulose (CMC, Tokyo Kasei Kogyo Co., Ltd.) is incubated for a certain time period and the amount of reducing sugar released is measured, the amount of enzyme producing the reducing sugar corresponding to 1 μlmol of glucose per minute, is defined as 1 unit.

EXAMPLE 1

Comparison Among Improvement Ratios of Fuzz-Removing Activities of Various Types of Cellulases by Addition of Nonionic Surfactant The cultivation of Rhizopus oryzae, Mucor circinelloides and Phycomyces nitens, and the purification of RCE I, MCE I and PCE I endoglucanases from the cultures, were carried out by the method described in International Publication No. WO00/24879.

The cultivation of Humicola insolens [Humicola insolens MN200-1 which was deposited under accession No. FERM BP-5977 (original accession No. FERM P-15736, original accession date: Jul. 15, 1996) with the National Institute of Advanced Industrial Science and Technology, at the an Independent Administrative Institution under the Ministry of Economy, Trade and Industry, the former name: the National Institute of Bioscience and Human-Technology, Agency of Industrial Science and Technology], and the purification of NCE4 endoglucanase from the culture, were carried out by the method described in International Publication No. WO98/03640.

The cultivation of Trichoderma viride [Trichoderma viride MC300-1 which was deposited under accession No. FERM BP-6047 (original accession No. FERM P-15842, original accession date: Sep. 9, 1996) with the National Institute of Advanced Industrial Science and Technology, at the an Independent Administrative Institution under the Ministry of Economy, Trade and Industry, AIST Tsukuba Central 6, Higashi 1-1-1, Tsukuba, Ibaraki, Japan (postal code No. 305-8566), the former name: the National Institute of Bioscience and Human-Technology, Agency of Industrial Science and Technology] was carried out by the method described in International Publication No. WO98/54332.

Fuzz-removing treatment from a cotton knit fabric with fuzz formed in a large washer (a fabric of 6 cm×8 cm from Cotton Smooth Knit No. 3900, Nitto Boseki Co., Ltd. was dyed in brown by reactive dyeing in Tsuyatomo-Senko), was carried out using the obtained culture supernatant and uniformly purified various endoglucanases under the following conditions.

(Test Conditions)
Testing machine: Launder Meter L-20 (Daiei Kagaku Seiki MFG., Japan)
Temperature: 40° C.
Time: 120 minutes
Amount of reaction solution: 40 ml
Reaction pH: only the Trichoderma viride culture supernatant was adjusted at pH 4 (20 mM acetate buffer), all other enzyme solutions were adjusted at pH 6 (5 mM phosphate buffer) for reaction. All the buffers were prepared using deionized water.
Type and amount of nonionic surfactant: 100 μg/ml polyoxyethylene lauryl ether (NOF Corporation, product name: NissanNonion K-220, number of oxyethylene units added: 20, HLB: 16.2)

To the treating solution were added four of about 16 g rubber balls together with the enzyme solution.

The amount of the enzyme solution required to remove approximately 50% of the formed fuzz on the basis of visual evaluation was determined in each of both cases of adding and not adding the nonionic surfactant. Thereafter, a value was obtained by dividing the amount of the enzyme solution required to remove approximately 50% of the fuzz in the case of not adding the nonionic surfactant by the amount in the case of adding the nonionic surfactant, and the obtained value was defined as an improvement ratio of the fuzz-removing activity by the addition of the nonionic surfactant. The results are shown in Table 1.

TABLE 1

|  | Improvement ratio of fuzz-removing activity by addition of nonionic surfactant (fold) |
| --- | --- |
| Humicola insolens culture supernatant | 1.2 |
| Trichoderma viride culture supernatant | 1.33 |
| Purified NCE 4 | 1.5 |
| Purified RCE I | 4.0 |
| Purified MCE I | 6.0 |
| Purified PCE I | 4.0 |

From the results of Table 1, it is found that the fuzz-removing activity of RCE I, MCE I and PCE I, which are endoglucanases derived from Zygomycetes, is improved by the addition of the nonionic surfactant at a level far higher than other enzymes including cellulase derived from Humicola insolens or Trichoderma viride, which are previous findings.

EXAMPLE 2

Improvement Effect of Fuzz-Removing Activity of RCE I Expressed in Humicola by Addition of Various Nonionic Surfactants RCE I endoglucanase was expressed in Humicola insolens according to the method described in Examples D3 and 4 of International Publication No. WO00/24879. Fuzz-removing treatment from a cotton knit fabric with fuzz formed in a large washer (a fabric of 6 cm×8 cm from Cotton Smooth Knit No. 3900, Nitto Boseki Co., Ltd. was dyed in brown by reactive dyeing in Tsuyatomo-Senko), was carried out using the obtained culture supernatant under the following conditions.

(Test Conditions)
Testing machine: Launder Meter L-20 (Daiei Kagaku Seiki MFG., Japan)
Temperature: 40° C.
Time: 120 minutes
Amount of reaction solution: 40 ml
Reaction pH: pH 6 (5 mM phosphate buffer prepared with deionized water)
Amount of nonionic surfactants: 100 μg/ml
Type of nonionic surfactants: Refer to Table 2 as described below.

To the treating solution were added four of about 16 g rubber balls together with the enzyme solution.

TABLE 2

| Type of surfactants | Product names | Manufacturing companies |
| --- | --- | --- |
| Polyoxyethylene lauryl ether (number of oxyethylene units added: 4) | Brij-35 | Wako Pure Chemical Industries, Ltd. |
| Polyoxyethylene lauryl ether (number of oxyethylene units added: 20) | K-220 | NOF Corporation |
| Polyoxyethylene cetyl ether (number of oxyethylene units added: 8) | P-208 | NOF Corporation |
| Polyoxyethylene nonyl phenyl ether | Nonipol 100 | Sanyo Chemical Industries, Ltd. |
| Polyoxyethylene octyl phenyl ether | Triton X100 | Wako Pure Chemical Industries, Ltd. |
| Polyoxyethylene sorbitan monooleate | Tween 80 | Wako Pure Chemical Industries, Ltd. |
| Polyethylene glycol 4000 | PEG 4000 | Wako Pure Chemical Industries, Ltd. |
| Terephthalic acid tetraethylene glycol polymer | FR 550 | Goo Chemical Co., Ltd. |

The amount of the enzyme solution required to remove approximately 50% of the formed fuzz on the basis of visual evaluation was determined in each of both cases of adding and not adding each nonionic surfactant. Thereafter, a value was obtained by dividing the amount of the enzyme solution required to remove approximately 50% of the fuzz in the case of not adding the nonionic surfactant by the amount in the case of adding the nonionic surfactant, and the obtained value was defined as an improvement ratio of the fuzz-removing activity by the addition of the nonionic surfactant. The results are shown in Table 3.

TABLE 3

| Type of nonionic surfactants | Improvement ratio of fuzz-removing activity by addition of nonionic surfactants (fold) |
| --- | --- |
| Polyoxyethylene lauryl ether (number of oxyethylene units added: 4) | 3.0 |
| Polyoxyethylene lauryl ether (number of oxyethylene units added: 20) | 3.0 |
| Polyoxyethylene cetyl ether (number of oxyethylene units added: 8) | 2.0 |
| Polyoxyethylene nonyl phenyl ether | 3.0 |
| Polyoxyethylene octyl phenyl ether | 2.0 |
| Polyoxyethylene sorbitan monooleate | 2.0 |
| Polyethylene glycol 4000 | 2.0 |
| Terephthalic acid tetraethylene glycol polymer | 2.5 |

From the results of Table 3, it is found that the fuzz-removing activity of the culture supernatant obtained by expressing and secreting RCE I in *Humicola insolens* was improved by any of the above nonionic surfactants.

EXAMPLE 3

Improvement Effect of Fuzz-Removing Activity of RCE I Expressed in *Humicola* by Addition of Nonionic Surfactants with Various Concentrations RCE I endoglucanase was expressed in *Humicola insolens* according to the method described in Examples D3 and 4 of International Publication No. WO00/24879. Fuzz-removing treatment from a cotton knit fabric with fuzz formed in a large washer (a fabric of 6 cm×8 cm from Cotton Smooth Knit No. 3900, Nitto Boseki Co., Ltd. was dyed in brown by reactive dyeing in Tsuyatomo-Senko), was carried out using the obtained culture supernatant under the following conditions.

(Test Conditions)

Testing machine: Launder Meter L-20 (Daiei Kagaku Seiki MPG., Japan)
Temperature: 40° C.
Time: 120 minutes
Amount of reaction solution: 40 ml
Reaction pH: pH 6 (5 mM phosphate buffer prepared with deionized water)
Amount of nonionic surfactant: 10 to 10,000 µg/ml
Type of nonionic surfactant: polyoxyethylene lauryl ether (NOF Corporation, product name: NissanNonion K-220, number of oxyethylene units added: 20, HLB: 16.2)

To the treating solution were added four of about 16 g rubber balls together with the enzyme solution.

The amount of the enzyme solution required to remove approximately 50% of the formed fuzz on the basis of visual evaluation was determined in the case of adding the nonionic surfactant in each concentration. Thereafter, a value was obtained by dividing the amount of the enzyme solution required to remove approximately 50% of the fuzz in the case of not adding the nonionic surfactant, by the amount in the case of adding the nonionic surfactant in each concentration, and the obtained value was defined as an improvement ratio of the fuzz-removing activity by the addition of the nonionic surfactant in each concentration. The results are shown in Table 4.

TABLE 4

| Additive amount of nonionic surfactant (µg/ml) | Improvement ratio of fuzz-removing activity by addition of nonionic surfactant (fold) |
| --- | --- |
| 10 | 1.5 |
| 20 | 2.0 |
| 50 | 2.5 |
| 100 | 3.0 |
| 200 | 3.0 |
| 400 | 3.0 |
| 1000 | 3.0 |
| 2000 | 2.0 |
| 3000 | 1.5 |
| 5000 | 1.5 |
| 10000 | 1.5 |

From the results of Table 4, it is found that the fuzz-removing activity of the culture supernatant obtained by expressing and secreting RCE I in *Humicola insolens* was improved by the addition of the nonionic surfactant having a wide range of concentration from 10 to 10,000 µg/ml.

EXAMPLE 4

Production of RCE I Cellulase Preparation Comprising Nonionic Surfactant

After mixing the following raw materials, an appropriate amount of water was added thereto, and the mixture was kneaded. The obtained product was subjectetd to a disk pelleter for molding, and the product obtained by injection molding was converted in a particle form using a marumerizer (Fuji Paudal Co., Ltd.) followed by drying and sieving the product so as to obtain a granulated product.

| (Raw materials) | Mixing ratio (%) |
|---|---|
| S-220 (nonionic surfactant manufactured by NOF Corporation) | 10% |
| RCE I cellulase powder product | 10% |
| Magnesium chloride (Wako Pure Chemical Industries, Co., Ltd.) | 0.5% |
| Monopotassium phosphate (same as above) | 2% |
| Dipotassium phosphate (same as above) | 1% |
| Corn starch (Shikishima Starch Co.) | 76.5% |

The RCE I cellulase powder product was prepared by concentrating the culture supernatant of RCE I expressed in *Humicola insolens* using ultrafiltration, according to the method described in Examples D3 and 4 of International Publication No. WO00/24879, followed by spray drying.

All publications, patents and patent applications cited herein are incorporated herein by reference in their entirety.

INDUSTRIAL APPLICABILITY

The present invention provides a cellulase preparation having dramatically improved Zygomycetes-derived endoglucanase activity by adding a nonionic surfactant into the preparation. If the present cellulase preparation is used in the treatment of fabric such as the reduction of fuzz of cellulose-containing fabric, the improvement of touch and appearance, the color clarification, localized color variation or softening, the deinking of waste paper, or the processing of improving the freeness of paper pulp, each of the above treatments can be carried out with a less amount of enzyme, thereby significantly reducing cost.

The invention claimed is:

1. A cellulase preparation for enhanced fuss-removing activity comprising nonionic surfactant(s) together with a protein comprising the amino acid sequence of SEQ ID NO: 1.

2. A cellulase preparation for enhanced fuss-removing activity comprising nonionic surfactant(s) together with protein(s) encoded by
   DNA encoding the amino acid sequence of SEQ ID NO: 1 or
   DNA which is fully complementary to a DNA hybridizing to a DNA encoding a protein comprising the amino acid sequence of SEQ ID NO: 1 under conditions in which, using as a probe a full-length DNA sequence encoding the amino acid sequence of labeled RCE I, wherein pre-hybridization is carried out at 42° C. for 1 hour according to the method of the electrochemiluminescent (ECL) direct DNA/RNA labeling and detection system (Amersham), then the probe is added thereto followed by hybridization at 42° C. for 15 hours, and thereafter, the resultant product is washed twice with a solution containing 0.4% SDS, 6Murea and 0.5×SSC (SSC; 15 mM trisodium citrate, 150 mM sodium chloride) at 42° C. for 20 minutes and finally followed by washing the product twice with 5×SSC at room temperature for 10 minutes and which encodes a protein having endoglucanase activity.

3. The cellulase preparation according to claim 1 wherein the nonionic surfactant is polyoxyethylene alkylether, polyoxyethylene alkylphenylether, polyoxyethylene monofatty acid ester, polyoxyethylene sorbitan monofatty acid ester, sorbitan monofatty acid ester, polyethylene glycol, glycerol monofatty acid ester, polyglycerine fatty acid ester, alkyl glycoside, esters of polyethoxylated alkyl glycosides, alkyl dimethyl amine oxide, fatty acid diethanol amide, polyoxyethylene alkylamine, terephthalic acid tetraethylene glycol polymer, alkyl polyethylene glycol ether, nonyl phenol polyethylene glycol ether, or fatty acid ester of sucrose or glucose.

4. The cellulase preparation according to claim 1 comprising 0.1 to 50% by weight of nonionic surfactant(s).

5. The cellulase preparation according to claim 1, which is a non-dusting granule or stabilized liquid.

6. A detergent composition comprising the cellulase preparation according to claim 1 with detergent components.

7. A method of treating fabric which comprises treating cellulose-containing fabric with the cellulase preparation according to claim 1 so as to improve the properties of the fabric.

8. The method according to claim 7 wherein the improvement of the properties of the fabric is the color clarification.

9. The method according to claim 7 wherein the improvement of the properties of the fabric is the removal of fuzz.

10. The method according to claim 7 wherein the improvement of the properties of the fabric is the providing of stonewash-like appearance and texture.

11. The method according to claim 7 wherein the improvement of the properties of the fabric is the improvement of touch and appearance.

12. The method according to claim 7 wherein the improvement of the properties of the fabric is softening of the fabric.

13. The method according to claim 7 wherein nonionic surfactant(s) are present in a concentration of 10 to 10,000 mg/L in a reaction system.

14. The method according to claim 7 wherein the method is carried out through a step of soaking, washing or rinsing the fabric.

15. A method of deinking waste paper comprising a step of treating waste paper with the cellulase preparation according to claim 1 together with a deinking agent.

16. A method of improving the freeness of paper pulp comprising a step of treating paper pulp with the cellulase preparation according to claim 1.

17. The cellulase preparation according to claim 2 wherein the nonionic surfactant is polyoxyethylene alkylether, polyoxyethylene alkylphenylether, polyoxyethylene monofatty acid ester, polyoxyethylene sorbitan monofatty acid ester, sorbitan monofatty acid ester, polyethylene glycol, glycerol inonofatty acid ester, polyglycerine fatty acid ester, alkyl glycoside, eaters of polyethoxylatecl alkyl glycosides, ailcyl dimethyl amine oxide, fatty acid diethanol amide, polyoxyothylene alkylamine, terephthalic acid tetraethylene glycol polymer, alkyl polyethylene glycol ether, nonyl phenol polyethylene glycol ether, or fatty acid ester of sucrose or glucose.

18. The cellulase preparation according to claim 2 comprising 0.1 to 50% by weight of nonionic surfactant(s).

19. The cellulase preparation according to claim 2, which is a non-dusting granule or stabilized liquid.

20. A detergent composition comprising the cellulase preparation according to claim 2 with detergent components.

21. A method of treating fabric which comprises treating cellulose-containing fabric with the ceflulase preparation according to claim 2 so as to improve the properties of the fabric.

22. The method according to claim 21 wherein the improvement of the properties of the fabric is the color clarification.

23. The method according to claim 21 wherein the improvement of the properties of the fabric is the removal of fuzz.

24. The method according to claim 21 wherein the improvement of the properties of the fabric is the providing of stonewash-like appearance and texture.

25. The method according to claim 21 wherein the improvement of the properties of the fabric is the improvement of touch and appearance.

26. The method according to claim 21 wherein the improvement of the properties of the fabric is softening of the fabric.

27. The method according to claim 21 wherein nonionic surfactant(s) are present in a concentration of 10 to 10,000 mg/b in a reaction system.

28. The method according to claim 21 wherein the method is carried out trough a step of soaking, washing or rinsing the fabric.

29. A method of deinking waste paper comprising a step of treating waste paper with the cellulase preparation according to claim 2 together with a deinking agent.

30. A method of improving the freeness of paper pulp comprising a step of treating paper pulp with the celiulase preparation according to claim 2.

* * * * *

SEQUENCE LISTING

```
<160> NUMBER OF SEQ ID NOS: 8

<210> SEQ ID NO 1
<211> LENGTH: 338
<212> TYPE: PRT
<213> ORGANISM: Rhizopus oryzae CP96001
<220> FEATURE:
<221> NAME/KEY: sig_peptide
<222> LOCATION: (-23)...(-1)
<220> FEATURE:
<221> NAME/KEY: mat_peptide
<222> LOCATION: (1)...(315)

<400> SEQUENCE: 1

Met Lys Phe Ile Thr Ile Ala Ser Ser Ala Leu Leu Ala Leu Ala Leu
            -20                 -15                 -10

Gly Thr Glu Met Ala Ser Ala Ala Glu Cys Ser Lys Leu Tyr Gly Gln
         -5                   1               5

Cys Gly Gly Lys Asn Trp Asn Gly Pro Thr Cys Cys Glu Ser Gly Ser
 10                  15                  20                  25

Thr Cys Lys Val Ser Asn Asp Tyr Tyr Ser Gln Cys Leu Pro Ser Gly
                 30                  35                  40

Ser Ser Gly Asn Lys Ser Ser Glu Ser Ala His Lys Lys Thr Thr Thr
                 45                  50                  55

Ala Ala His Lys Lys Thr Thr Thr Ala Ala His Lys Lys Thr Thr Thr
                 60                  65                  70

Ala Pro Ala Lys Lys Thr Thr Thr Val Ala Lys Ala Ser Thr Pro Ser
     75                  80                  85

Asn Ser Ser Ser Ser Ser Gly Lys Tyr Ser Ala Val Ser Gly Gly
 90                  95                 100                 105

Ala Ser Gly Asn Gly Val Thr Thr Arg Tyr Trp Asp Cys Cys Lys Ala
                110                 115                 120

Ser Cys Ser Trp Pro Gly Lys Ala Asn Val Ser Ser Pro Val Lys Ser
                125                 130                 135

Cys Asn Lys Asp Gly Val Thr Ala Leu Ser Asp Ser Asn Ala Gln Ser
                140                 145                 150

Gly Cys Asn Gly Gly Asn Ser Tyr Met Cys Asn Asp Asn Gln Pro Trp
                155                 160                 165
```

```
Ala Val Asn Asp Asn Leu Ala Tyr Gly Phe Ala Ala Ala Ile Ser
170                 175                 180                 185

Gly Gly Gly Glu Ser Arg Trp Cys Cys Ser Cys Phe Glu Leu Thr Phe
            190                 195                 200

Thr Ser Thr Ser Val Ala Gly Lys Lys Met Val Val Gln Val Thr Asn
        205                 210                 215

Thr Gly Gly Asp Leu Gly Ser Ser Thr Gly Ala His Phe Asp Leu Gln
        220                 225                 230

Met Pro Gly Gly Val Gly Ile Phe Asn Gly Cys Ser Ser Gln Trp
    235                 240                 245

Gly Ala Pro Asn Asp Gly Trp Gly Ser Arg Tyr Gly Gly Ile Ser Ser
250                 255                 260                 265

Ala Ser Asp Cys Ser Ser Leu Pro Ser Ala Leu Gln Ala Gly Cys Lys
            270                 275                 280

Trp Arg Phe Asn Trp Phe Lys Asn Ala Asp Asn Pro Ser Met Thr Tyr
            285                 290                 295

Lys Glu Val Thr Cys Pro Lys Glu Ile Thr Ala Lys Thr Gly Cys Ser
        300                 305                 310

Arg Lys
    315

<210> SEQ ID NO 2
<211> LENGTH: 366
<212> TYPE: PRT
<213> ORGANISM: Rhizopus oryzae CP96001
<220> FEATURE:
<221> NAME/KEY: sig_peptide
<222> LOCATION: (-23)...(-1)
<220> FEATURE:
<221> NAME/KEY: mat_peptide
<222> LOCATION: (1)...(343)

<400> SEQUENCE: 2

Met Lys Phe Ile Thr Ile Thr Ser Ser Ala Leu Leu Ala Leu Ala Leu
            -20                 -15                 -10

Gly Thr Glu Met Ala Ser Ala Ala Lys Cys Ser Lys Leu Tyr Gly Gln
        -5                   1                   5

Cys Gly Gly Lys Asp Trp Asn Gly Pro Thr Cys Cys Glu Ser Gly Ser
10                  15                  20                  25

Thr Cys Lys Val Ser Asn Asp Tyr Tyr Ser Gln Cys Leu Ala Pro Glu
            30                  35                  40

Ser Asn Gly Asn Lys Ser Ser Glu Cys Ser Lys Leu Tyr Gly Gln Cys
            45                  50                  55

Gly Gly Lys Asp Trp Asn Gly Pro Thr Cys Cys Glu Ser Gly Ser Thr
        60                  65                  70

Cys Lys Val Ser Asn Asp Tyr Tyr Ser Gln Cys Leu Ala Pro Glu Ser
    75                  80                  85

Asn Gly Asn Lys Thr Ser Glu Ser Ala His Lys Thr Thr Thr Thr Thr
90                  95                  100                 105

Ala Pro Ala Lys Glu Ile Thr Thr Ala Lys Ala Ser Asn Ser Ser
            110                 115                 120

Asn Ser Ser Gly Lys Tyr Ser Ile Val Ser Gly Ala Ser Gly Asn
        125                 130                 135

Gly Val Thr Thr Arg Tyr Trp Asp Cys Cys Lys Ala Ser Cys Ser Trp
        140                 145                 150

Pro Gly Lys Ala Asn Val Ser Ser Pro Val Lys Ser Cys Asn Lys Asp
    155                 160                 165
```

-continued

```
Gly Val Thr Ala Leu Ser Asp Ser Asn Val Gln Ser Gly Cys Asn Gly
170                 175                 180                 185

Gly Asn Ser Tyr Met Cys Asn Asp Asn Gln Pro Trp Ala Val Asn Asp
                190                 195                 200

Asn Leu Ala Tyr Gly Phe Ala Ala Ala Ile Ser Gly Gly Gly Glu
                205                 210                 215

Ser Arg Trp Cys Cys Ser Cys Phe Glu Leu Thr Phe Thr Ser Thr Ser
            220                 225                 230

Val Ala Gly Lys Lys Met Val Ile Gln Val Thr Asn Thr Gly Gly Asp
        235                 240                 245

Leu Gly Ser Ser Thr Gly Ala His Phe Asp Leu Gln Met Pro Gly Gly
250                 255                 260                 265

Gly Val Gly Ile Phe Asn Gly Cys Ser Lys Gln Trp Gly Ala Pro Asn
                270                 275                 280

Asp Gly Trp Gly Ser Arg Tyr Gly Gly Ile Ser Ser Ala Ser Asp Cys
            285                 290                 295

Ser Ser Leu Pro Ser Ala Leu Gln Ala Gly Cys Lys Trp Arg Phe Asn
        300                 305                 310

Trp Phe Lys Asn Ala Asp Asn Pro Ser Met Thr Tyr Lys Glu Val Thr
    315                 320                 325

Cys Pro Lys Glu Ile Thr Ala Lys Thr Gly Cys Ser Arg Lys
330                 335                 340

<210> SEQ ID NO 3
<211> LENGTH: 360
<212> TYPE: PRT
<213> ORGANISM: Rhizopus oryzae CP96001
<220> FEATURE:
<221> NAME/KEY: sig_peptide
<222> LOCATION: (-23)...(-1)
<220> FEATURE:
<221> NAME/KEY: mat_peptide
<222> LOCATION: (1)...(337)

<400> SEQUENCE: 3

Met Lys Phe Leu Thr Ile Ala Ser Ser Ala Ile Leu Ala Leu Ala Val
                -20                 -15                 -10

Gly Thr Glu Met Ala His Ala Ala Glu Cys Ser Lys Ala Tyr Tyr Gln
        -5                   1                   5

Cys Gly Gly Lys Asn Trp Asp Gly Pro Thr Cys Cys Glu Ser Gly Ser
10                  15                  20                  25

Thr Cys Val Asp Tyr Pro Asp Asn Pro Phe Tyr Ser Gln Cys Val Pro
                30                  35                  40

Asn Glu Asn Leu Thr Ser Thr Asn Lys Ser Ser His Lys Thr Thr Thr
                45                  50                  55

Thr Glu Ser Ala Lys Lys Thr Thr Thr Lys Gly Ser Lys Thr
            60                  65                  70

Thr Thr Thr Glu Ala Ser Lys Lys Thr Thr Thr Glu Ala Ser Lys
        75                  80                  85

Lys Thr Thr Thr Thr Glu Ala Ser Lys Lys Thr Thr Thr Thr Lys
90                  95                  100                 105

Lys Ala Ser Thr Ser Thr Ser Ser Ser Ser Ala Ser Thr Asn
                110                 115                 120

Tyr Ser Ala Val Ser Gly Gly Ala Ser Gly Asn Gly Glu Thr Thr Arg
                125                 130                 135

Tyr Trp Asp Cys Cys Lys Pro Ser Cys Ser Trp Pro Gly Lys Ala Asp
```

-continued

```
            140                 145                 150
Val Thr Ser Pro Val Gly Ser Cys Asn Lys Asp Gly Lys Thr Leu Ala
    155                 160                 165

Asp Asn Asn Thr Gln Asn Gly Cys Val Gly Gly Ser Ser Tyr Thr Cys
170                 175                 180                 185

Asn Asp Asn Gln Pro Trp Val Val Ser Asp Leu Ala Tyr Gly Phe
                190                 195                 200

Ala Ala Ala Ser Ile Ser Gly Gly Ser Glu Ala Thr Trp Cys Cys Ala
                205                 210                 215

Cys Phe Glu Leu Thr Phe Thr Ser Thr Ala Val Lys Gly Lys Lys Met
            220                 225                 230

Val Val Gln Val Thr Asn Thr Gly Ser Asp Leu Gly Ser Asn Thr Gly
    235                 240                 245

Ala His Phe Asp Leu Gln Met Pro Gly Gly Gly Val Gly Ile Tyr Asn
250                 255                 260                 265

Gly Cys Ala Thr Gln Trp Gly Ala Pro Thr Asp Gly Trp Gly Ala Arg
                270                 275                 280

Tyr Gly Gly Val Ser Ser Ala Ser Asp Cys Ser Asn Leu Pro Ser Ala
                285                 290                 295

Leu Gln Ala Gly Cys Lys Trp Arg Phe Gly Trp Phe Lys Asn Ala Asp
            300                 305                 310

Asn Pro Thr Met Thr Tyr Lys Gln Val Thr Cys Pro Lys Ala Ile Thr
    315                 320                 325

Ala Lys Ser Gly Cys Ser Arg Lys
330                 335
```

<210> SEQ ID NO 4
<211> LENGTH: 338
<212> TYPE: PRT
<213> ORGANISM: Mucor circinelloides CP99001
<220> FEATURE:
<221> NAME/KEY: sig_peptide
<222> LOCATION: (-22)...(-1)
<220> FEATURE:
<221> NAME/KEY: mat_peptide
<222> LOCATION: (1)...(316)

<400> SEQUENCE: 4

```
Met Lys Phe Thr Val Ala Ile Thr Ser Ile Ala Val Ala Leu Ala Leu
            -20                 -15                 -10

Ser Ser Ser Ala Glu Ala Ser Cys Ser Ser Val Tyr Gly Gln Cys
    -5                  1                   5                   10

Gly Gly Ile Gly Trp Ser Gly Pro Thr Cys Cys Glu Ser Gly Ser Thr
                15                  20                  25

Cys Val Ala Gln Glu Gly Asn Lys Tyr Tyr Ser Gln Cys Leu Pro Gly
                30                  35                  40

Ser His Ser Asn Ala Gly Asn Ala Ser Ser Thr Lys Lys Thr Ser
        45                  50                  55

Thr Lys Thr Ser Thr Thr Thr Ala Lys Ala Thr Ala Thr Val Thr Thr
    60                  65                  70

Lys Thr Val Thr Lys Thr Thr Lys Thr Thr Thr Lys Thr Ser Thr
75                  80                  85                  90

Thr Ala Ala Ala Ser Thr Ser Thr Ser Ser Ala Gly Tyr Lys Val
                95                  100                 105

Ile Ser Gly Gly Lys Ser Gly Ser Gly Ser Thr Thr Arg Tyr Trp Asp
            110                 115                 120
```

-continued

```
Cys Cys Lys Ala Ser Cys Ser Trp Pro Gly Lys Ala Ser Val Thr Gly
        125                 130                 135

Pro Val Asp Thr Cys Ala Ser Asn Gly Ile Ser Leu Leu Asp Ala Asn
140                 145                 150

Ala Gln Ser Gly Cys Asn Gly Asn Gly Phe Met Cys Asn Asn Asn
155                 160                 165                 170

Gln Pro Trp Ala Val Asn Asp Glu Leu Ala Tyr Gly Phe Ala Ala Ala
                175                 180                 185

Ser Ile Ala Gly Ser Asn Glu Ala Gly Trp Cys Cys Gly Cys Tyr Glu
                190                 195                 200

Leu Thr Phe Thr Ser Gly Ala Ala Ser Gly Lys Lys Met Val Val Gln
        205                 210                 215

Val Thr Asn Thr Gly Gly Asp Leu Gly Ser Asn His Phe Asp Leu Gln
    220                 225                 230

Met Pro Gly Gly Gly Val Gly Ile Phe Asn Gly Cys Ala Ala Gln Trp
235                 240                 245                 250

Gly Ala Pro Asn Asp Gly Trp Gly Ala Arg Tyr Gly Gly Val Ser Ser
                255                 260                 265

Val Ser Asp Cys Ala Ser Leu Pro Ser Ala Leu Gln Ala Gly Cys Lys
                270                 275                 280

Trp Arg Phe Asn Trp Phe Lys Asn Ser Asp Asn Pro Thr Met Thr Phe
        285                 290                 295

Lys Glu Val Thr Cys Pro Ala Glu Leu Thr Thr Arg Ser Gly Cys Glu
    300                 305                 310

Arg Lys
315

<210> SEQ ID NO 5
<211> LENGTH: 387
<212> TYPE: PRT
<213> ORGANISM: Mucor circinelloides CP99001
<220> FEATURE:
<221> NAME/KEY: sig_peptide
<222> LOCATION: (-22)...(-1)
<220> FEATURE:
<221> NAME/KEY: mat_peptide
<222> LOCATION: (1)...(365)

<400> SEQUENCE: 5

Met Lys Phe Thr Val Ala Ile Thr Ser Ile Ala Val Ala Leu Ala Leu
        -20                 -15                 -10

Ser Ser Ser Ala Glu Ala Ala Ser Cys Ser Ser Val Tyr Gly Gln Cys
    -5                   1                   5                  10

Gly Gly Ile Gly Trp Thr Gly Pro Thr Cys Cys Asp Ala Gly Ser Thr
                 15                  20                  25

Cys Lys Ala Gln Lys Asp Asn Lys Tyr Tyr Ser Gln Cys Ile Pro Lys
             30                  35                  40

Pro Lys Gly Ser Ser Ser Ser Ser Cys Ser Ser Val Tyr Ser Gln
                45                  50                  55

Cys Gly Gly Ile Gly Trp Ser Gly Pro Thr Cys Cys Glu Ser Gly Ser
60                  65                  70

Thr Cys Val Ala Gln Glu Gly Asn Lys Tyr Tyr Ser Gln Cys Leu Pro
75                  80                  85                  90

Gly Ser His Ser Asn Asn Ala Gly Asn Ala Ser Ser Thr Lys Lys Thr
                95                  100                 105

Ser Thr Lys Thr Ser Thr Thr Thr Ala Lys Ala Thr Ala Thr Val Thr
            110                 115                 120
```

```
Thr Lys Thr Val Thr Lys Thr Thr Thr Lys Thr Thr Thr Lys Thr Ser
        125                 130                 135
Thr Thr Ala Ala Ala Ser Thr Ser Thr Ser Ser Ser Ala Gly Tyr Lys
    140                 145                 150
Val Ile Ser Gly Gly Lys Ser Gly Ser Gly Ser Thr Thr Arg Tyr Trp
155                 160                 165                 170
Asp Cys Cys Lys Ala Ser Cys Ser Trp Pro Gly Lys Ala Ser Val Thr
                175                 180                 185
Gly Pro Val Asp Thr Cys Ala Ser Asn Gly Ile Ser Leu Leu Asp Ala
                190                 195                 200
Asn Ala Gln Ser Gly Cys Asn Gly Gly Asn Gly Phe Met Cys Asn Asn
                205                 210                 215
Asn Gln Pro Trp Ala Val Asn Asp Glu Leu Ala Tyr Gly Phe Ala Ala
            220                 225                 230
Ala Ser Ile Ala Gly Ser Asn Glu Ala Gly Trp Cys Cys Gly Cys Tyr
235                 240                 245                 250
Glu Leu Thr Phe Thr Ser Gly Ala Ala Ser Gly Lys Lys Met Val Val
                255                 260                 265
Gln Val Thr Asn Thr Gly Gly Asp Leu Gly Ser Asn His Phe Asp Leu
            270                 275                 280
Gln Met Pro Gly Gly Gly Val Gly Ile Phe Asn Gly Cys Ala Ala Gln
            285                 290                 295
Trp Gly Ala Pro Asn Asp Gly Trp Gly Ala Arg Tyr Gly Gly Val Ser
300                 305                 310
Ser Val Ser Asp Cys Ala Ser Leu Pro Ser Ala Leu Gln Ala Gly Cys
315                 320                 325                 330
Lys Trp Arg Phe Asn Trp Phe Lys Asn Ser Asp Asn Pro Thr Met Thr
                335                 340                 345
Phe Lys Glu Val Thr Cys Pro Ala Glu Leu Thr Thr Arg Ser Gly Cys
            350                 355                 360
Glu Arg Lys
        365

<210> SEQ ID NO 6
<211> LENGTH: 346
<212> TYPE: PRT
<213> ORGANISM: Phycomyces nitens CP99002
<220> FEATURE:
<221> NAME/KEY: sig_peptide
<222> LOCATION: (-19)...(-1)
<220> FEATURE:
<221> NAME/KEY: mat_peptide
<222> LOCATION: (1)...(327)

<400> SEQUENCE: 6

Met Lys Phe Ser Ile Ile Ala Ser Ala Leu Leu Leu Ala Ala Ser Ser
                -15                 -10                 -5
Thr Tyr Ala Ala Glu Cys Ser Gln Gly Tyr Gly Gln Cys Gly Gly Lys
        1               5                   10
Met Trp Thr Gly Pro Thr Cys Cys Thr Ser Gly Phe Thr Cys Val Gly
        15                  20                  25
Ala Glu Asn Asn Glu Trp Tyr Ser Gln Cys Ile Pro Asn Asp Gln Val
30                  35                  40                  45
Gln Gly Asn Pro Lys Thr Thr Thr Thr Thr Lys Ala Ala Thr
            50                  55                  60
Thr Thr Lys Ala Pro Val Thr Thr Thr Lys Ala Thr Thr Thr Thr Thr
```

-continued

```
                        65                    70                    75
    Thr Lys Ala Pro Val Thr Thr Thr Lys Ala Thr Thr Thr Thr Thr
                 80                    85                    90

Lys Thr Thr Thr Lys Thr Thr Thr Thr Lys Ala Ala Thr Thr Ser
             95                   100                   105

Ser Ser Asn Thr Gly Tyr Ser Pro Ile Ser Gly Phe Ser Gly Asn
    110                 115                 120                 125

Gly Arg Thr Thr Arg Tyr Trp Asp Cys Cys Lys Pro Ser Cys Ala Trp
                    130                 135                 140

Asp Gly Lys Ala Ser Val Thr Lys Pro Val Leu Thr Cys Ala Lys Asp
                145                 150                 155

Gly Val Ser Arg Leu Gly Ser Asp Val Gln Ser Gly Cys Val Gly Gly
                160                 165                 170

Gln Ala Tyr Met Cys Asn Asp Asn Gln Pro Trp Val Asn Asp Asp
    175                 180                 185

Leu Ala Tyr Gly Phe Ala Ala Ala Ser Leu Gly Ser Ala Gly Ala Ser
    190                 195                 200                 205

Ala Phe Cys Cys Gly Cys Tyr Glu Leu Thr Phe Thr Asn Thr Ala Val
                    210                 215                 220

Ala Gly Lys Lys Phe Val Val Gln Val Thr Asn Thr Gly Asp Asp Leu
                225                 230                 235

Ser Thr Asn His Phe Asp Leu Gln Met Pro Gly Gly Gly Val Gly Tyr
                240                 245                 250

Phe Asn Gly Cys Gln Ser Gln Trp Asn Thr Asn Thr Asp Gly Trp Gly
    255                 260                 265

Ala Arg Tyr Gly Gly Ile Ser Ser Ile Ser Glu Cys Asp Lys Leu Pro
    270                 275                 280                 285

Thr Gln Leu Gln Ala Gly Cys Lys Trp Arg Phe Gly Trp Phe Lys Asn
                    290                 295                 300

Ala Asp Asn Pro Glu Val Thr Phe Lys Ala Val Thr Cys Pro Ala Glu
                305                 310                 315

Ile Ile Ala Lys Thr Gly Cys Glu Arg Lys
                320                 325
```

<210> SEQ ID NO 7
<211> LENGTH: 1257
<212> TYPE: DNA
<213> ORGANISM: Humicola insolens
<220> FEATURE:
<221> NAME/KEY: intron
<222> LOCATION: (453)..(509)

<400> SEQUENCE: 7

```
aatgacgggg caacctcccg cccgggccca actcttgggt ttggtttgac aggccgtctg      60
tctcttgcgt cctcttacta cgcctgcctg gaccctacgt ctcaactccg attcaagatg     120
cgttcctccc ctctcctccg ctccgccgtt gtggccgccc tgccggtgtt ggcccttgcc     180
gctgatggca agtccacccg ctactgggac tgctgcaagc cttcgtgcgg ctgggccaag     240
aaggctcccg tgaaccagcc tgtcttctcc tgcaacgcca acttccagcg tctcactgac     300
ttcgacgcca gtccggctg cgagccgggc ggtgtcgcct actcgtgcgc cgaccagacc     360
ccatgggctg tgaacgacga cttcgcgttc ggttttgctg ccacctctat tgccggcagc     420
aatgaggcgg gctggtgctg cgcctgctac gagtaagctt tggtcgcgtg tgtaacactg     480
tgcaggcata gcactaacca cctcccaggc tcaccttcac atccggtcct gttgctggca     540
```

```
agaagatggt cgtccagtcc accagcactg gcggtgatct tggcagcaac cacttcgatc    600
tcaacatccc cggcggcggc gtcggcatct tcgacggatg cactcccag ttcggcggtc     660 tgcccggcca cgctacggc ggcatctcgt cccgcaacga gtgcgatcgg ttccccgacg     720
ccctcaagcc cggctgctac tggcgcttcg actggttcaa gaacgccgac aacccgagct    780
tcagcttccg tcaggtccaa tgcccagccg agctcgtcgc tcgcaccgga tgccgccgca    840
acgacgacgg caacttccct gccgtccaga tcccctccag cagcaccagc tctccggtcg    900
gccagcctac cagtaccagc accacctcca cctccaccac ctcgagcccg cccgtccagc    960
ctacgactcc cagcggctgc actgctgaga ggtgggctca gtgcggcggc aatggctgga    1020
gcggctgcac cacctgcgtc gctggcagca cctgcacgaa gattaatgac tggtaccatc    1080
agtgcctgta acgcaggc agcctgagaa ccttactggt tgcgcaacga aatgacactc     1140
ccaatcactg tattagttct tgtacataat ttcgtcatcc ctccagggat tgtcacatat    1200
atgcaatgat gaatactgaa cacaaacctg gccgcttgaa ctggccgaag gaatgcc      1257
```

<210> SEQ ID NO 8
<211> LENGTH: 1720
<212> TYPE: DNA
<213> ORGANISM: Trichoderma viride
<220> FEATURE:
<221> NAME/KEY: intron
<222> LOCATION: (500)..(682)

<400> SEQUENCE: 8

```
ggtgtgtcat ttctcctcaa catactgcct ttcaacaact ttcgcctcct ccctggcctg     60
atatcccaat atcagttttt cccaaagtag caagtcatca gtaaatctgc tcatctatca    120
ttaatcagtg cccatagtgt ctgtctgttg attgcctccc gccatacacg atgaacagga    180
ccatggctcc attgctgctt gcagcgtcga tactcttcgg gggcgctgct gcacaacaga    240
ctgtctgggg acagtgtgga ggtattggtt ggagcggacc tacgagttgt gctcctggat    300
cagcttgttc tactctcaat ccttattatg cgcaatgcat tccgggggcc actagtatca    360
ccacctcgac ccgaccccc tcgggtccaa ccaccaccac cagagccacc tcaacgacct    420
catctccgcc accgaccagc tctggagttc gatttgctgg cgttaacatc gcgggctttg    480
acttcggatg taccacagag tatgtcttca tgttgcatag tgttgctggc tgagtattct    540
gggcggatga tttatagctg tgcgggctgc aaaacaccgc cggtctgcca ctatcaaggc    600
atagttgata ggcggcggtg tttcttcaa tcccctgatt acactctcaa gaatctagtg     660
gctgatggat gtatgattac agtggcactt gcgttacatc gaaggtttat cctccgttga    720
agaacttcac tggggcaaac aactacccgg acggtatcgg ccagatgcag cacttcgtca    780
acgatgatgg gatgactatt tccgcctac ccgtcggatg gcagtacctc gtaaacaaca     840
atctgggtgg aactctcgat tccaccagta tctcgaagta tgatcagctc gttcaggggt    900
gcctgtctct cggtgtatac tgcatcatcg acatccacaa ttatgctcga tggaacggtg    960
gaatcattgg ccaggaggc cctacaaatg cccagtttac cagtctttgg tcgcagttgg    1020
catcgaagta cgcgtctcag tcgagggtgt ggttcggaat aatgaatgag ccccacgacg    1080
tgaacatcaa cacttgggct gccacggttc aagaggtcgt cactgcaatc cgcaacgccg    1140
gtgctacgtc gcaatacatt tctctgcctg gaaatgatta tcaatctgcg gcagctttta    1200
tttccgatgg cagtgcagcc gccctgtctc aggtaacgaa ccctgatgga tcaacaacga    1260
atctaatctt cgatgtccac aagtacttag actcggacaa ctccggtact cacgccgaat    1320
```

-continued

```
gcactacaaa caacatcgac ggcgcctttg ctcctctcgc cacttggctt cgacagaaca    1380
accgccaggc tattctgacg gaaaccggcg gtggcaatgt tcagtcctgc atccaagatt    1440
tgtgccaaca gatccagtac ctcaaccaga actcagatgt ctatcttggc tatgctggct    1500
ggggtgccgg ttcatttgat agcacttata ttctgacgga aacgcctact ggaagcggta    1560
actcgtggac ggacacatcc ctagttagct cgtgtctcgc caggaagtaa caccgaggtc    1620
gattgcagga gccttgtcaa tagcgatttc atcttgctgt acataattct tactctctga    1680
agccgcttgt tctgggtatg tgtcttgaca ggtttctaga                          1720
```